United States Patent [19]

Davidson et al.

[11] 4,282,159

[45] Aug. 4, 1981

[54] PREPARATION OF ALKYLENE OXIDES

[75] Inventors: Robert S. Davidson; Richard A. Grieger-Block, both of Madison, Wis.

[73] Assignee: Wisconsin Alumni Research Foundation, Madison, Wis.

[21] Appl. No.: 117,542

[22] Filed: Feb. 1, 1980

Related U.S. Application Data

[63] Continuation of Ser. No. 916,480, Jun. 19, 1978, abandoned.

[51] Int. Cl.$^3$ .................. C07D 301/26; C07J 9/00
[52] U.S. Cl. .................. 260/348.21; 260/239.55 R; 260/348.18; 260/348.22
[58] Field of Search .................. 260/348.21, 348.22, 260/348.18, 239.55 R

[56] References Cited

U.S. PATENT DOCUMENTS 3,548,012  12/1970  Cornforth .................. 260/348.21

OTHER PUBLICATIONS

Sigwart, C. et al., Helv. Chim. Acta (1970), vol. 53(1), pp.177–185.
Chemical Abstracts, vol. 80 (1974) 100627e.
Chemical Abstracts, vol. 65 (1966) 78b.
Chemical Abstracts, vol. 77 (1972) 144275f.
Chemical Abstracts, vol. 79 (1973) 142554p.

*Primary Examiner*—Norma S. Milestone
*Attorney, Agent, or Firm*—McDougall, Hersh & Scott

[57] ABSTRACT

The preparation of propylene oxide or other epoxides by reaction which comprises the introduction of oxygen and olefin as reaction ingredients and the removal of the epoxide as it is formed in which iodine reacts with the olefin in a first reaction step to form iodohydrin and hydrogen iodide, converting the iodohydrin to the epoxide with the further production of hydrogen iodide in a second reaction step, and converting the hydrogen iodide to iodine for recycle to the first reaction step in a third reaction step in which an imidazole-copper complex is used as a catalyst in the third reaction step and which finds beneficial use in the first and second reaction steps to enable joinder of said reaction steps.

23 Claims, 1 Drawing Figure

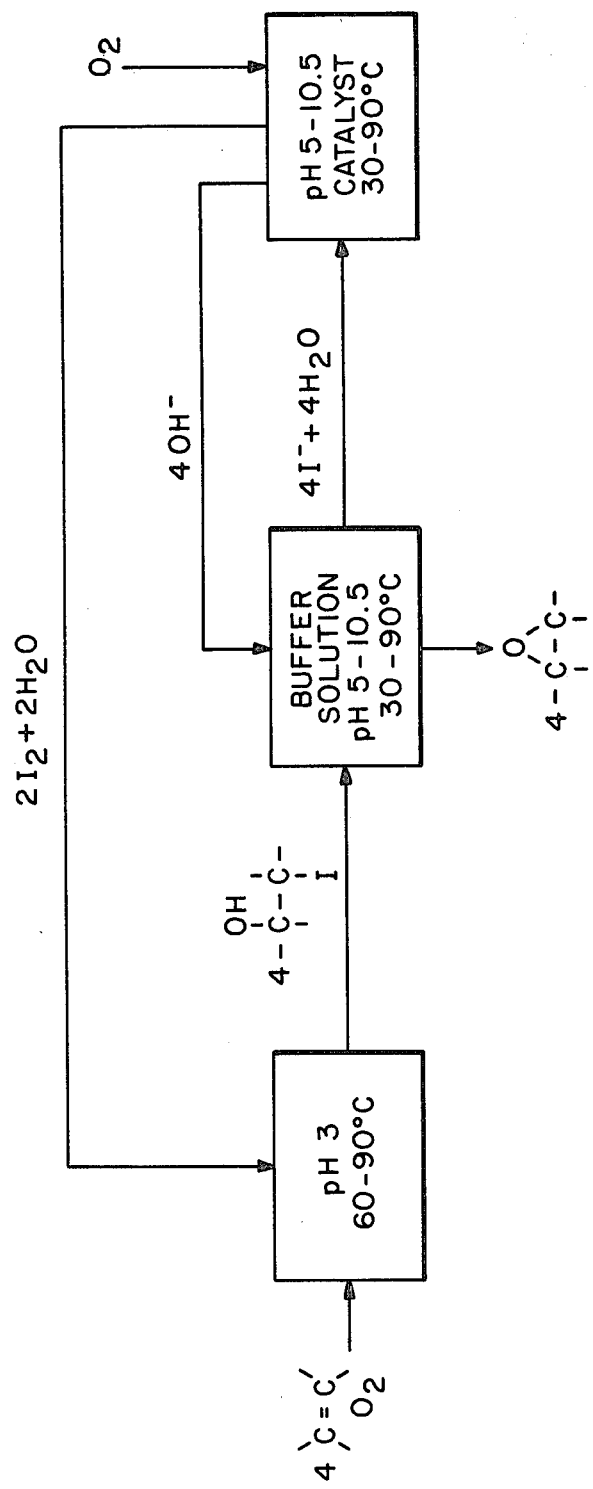

PREPARATION OF ALKYLENE OXIDES

This is a continuation of application Ser. No. 916,480, filed June 19, 1978, now abandoned.

This invention relates to a process for production of propylene oxide or other epoxides from corresponding olefins and it relates more particularly to a process which offers high conversion from the olefin as well as minimum consumption of other materials.

Ethylene oxide has been prepared by reaction of ethylene in the gaseous phase in the presence of silver oxidation catalyst. Attempts to make use of the same reaction to prepare propylene oxide have resulted in yields so low as to be uneconomical.

In another process, referred to as the Oxirane process, isobutane or ethylbenzene is reacted with oxygen in the presence of a catalyst to produce the corresponding hydroperoxide which is then reacted with propylene on a substantially equi-molecular basis to yield tert-butyl alcohol, or methyl phenyl carbinol and propylene oxide in about a 90% conversion.

In U.S. Pat. No. 2,856,417, description is made of a process which makes use of chlorine for the production of chlorohydrin. This is found to be objectionable because of the use of chlorine and production of large amounts of an undesirable salt.

It is an object of this invention to provide a more efficient process for the preparation of propylene oxide, one which does not produce unwanted byproducts and one in which materials employed in the process can be reused or recycled and one which produces a high yield, thereby materially to reduce the cost of the product.

The invention will be described with reference to the preparation of propylene oxide from propylene, it being understood that other olefins can be substituted for propylene to produce the corresponding oxides in accordance with the practice of this invention.

Such other olefins include aliphatic substituted-hydrocarbon olefinic compounds having from 3-20 carbon atoms wherein the atoms other than carbon and hydrogen are halogens or oxygen, especially oxygen incorporated as functional groups such as hydroxy, alkoxy, aryloxy or carboalkoxy or wherein the halogen is not substituted on the olefinic double bond, as represented by allyl chloride, allyl bromide, 1-chlorobutene-2, 1,4-dichlorobutene-2, 3-bromobutene-1, 4-chlorobutene-1, 3-chloropentene-1 and 4-chlorohexene-2, as representative of the halogen substituted olefinic compounds and allyl alcohol, oleyl alcohol, abietyl alcohol, cholesterol, olefinic unsaturated aliphatic esters such as methyl oleate, butyl acrylate and 2-ethyl hexylmethacrylate as representative of the oxygen containing olefinic compounds. However, the preferred practice of the invention is with hydrocarbon olefinic compounds containing only carbon and hydrogen and preferably aliphatic or aromatic hydrocarbons having at least one carbon-to-carbon double bond in an aliphatic linkage, in a non-aromatic carbon-to-carbon double bond.

Such olefinic hydrocarbons can be represented by aliphatic monoolefins having from 3-20 carbon atoms such as alkenes (straight or branched) as represented by propylene, 1-butene, 2-butene, isoamylene, 1-pentene, 2-hexene, 5-methyl-octene, etc.; cyclic monoolefins such as cycloalkenes represented by 1-methylcyclopentene, cyclohexene, bicyclo (2,2,1) hept-2-ene, cyclododecene and the like; alkenyl cycloalkanes, such as vinyl cyclopentane, 2-butenyl-cyclohexane and the like. Preferred are the monoolefinic compounds wherein one of the double bond carbons has two hydrogen groups such as in the alpha olefins of which propylene is most preferred. Included also are the diolefins and other polyolefins, such as the butadienes, hexatriene, and the like.

In a first reaction, propylene is reacted with iodine in the presence of water at a pH below 3 and at a temperature within the range of 60°–90° C. to produce iodohydrin and the acid hydrogen iodide. When air is bubbled through the reaction medium, the acid hydrogen iodide is converted to iodine which can react with more propylene. This is significant for the reason that it reduces the amount of iodine required by about 50%.

In a second reaction, the iodohydrin is reacted in a buffer solution at pH 5–10.5 and at a temperature within the range of 30°–90° C. to produce propylene oxide as product and the acid hydrogen iodide.

In a third reaction, the acid hydrogen iodide from the second reaction is oxidized with oxygen at pH of 5–10.5 and at 30°–90° C., in the presence of a catalyst to convert the hydrogen iodide to iodine that can be recycled to the first reaction.

The reaction route to the epoxide is illustrated by the following system, which calls for a net input of the olefin and oxygen, as shown in the flow diagram of the drawing.

IODOHYDRIN ROUTE TO EPOXIDES

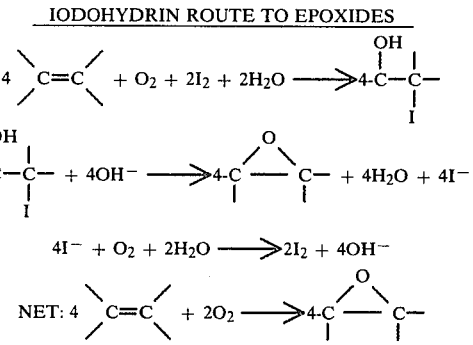

It will be apparent from the above scheme of the described reactions that the propylene is reacted to yield the desired product of propylene oxide and that the hydrogen iodides generated in the first and second reactions are reconverted to iodine for recycle as feed for reaction with the propylene in the first reaction. Thus the only consumable ingredient besides propylene is oxygen, which is freely available when use is made of air as the oxygen-containing gas. The described reaction proceeds at high yield and with little if any side reaction or by-products being formed, thereby permitting full and easy recovery of the epoxide and recycle of other constituents.

The first reaction of iodine with the olefinic compound to form the iodohydrin and hydrogen iodide is substantially the same as that described in U.S. Pat. No. 3,548,012. The iodine and the olefinic compound are reacted in the presence of water at a temperature within the range of 60°–90° C. It is preferred to carry out the reaction in a solvent mixture of water and an organic liquid in which the olefinic compound is soluble and which is miscible with water so that all of the reactants can be retained in a single phase.

As an organic liquid, it is preferred to make use of acetonitrile, dioxane, sulfolane or dimethyl sulfoxide (DMSO), but other unreactive organic compounds which are liquid under the reaction conditions can be employed.

When use is made of an organic liquid, best results are secured when the organic liquid is employed in an amount greater than 1 part by volume organic liquid to 2 parts by volume water to 18 parts by volume organic liquid to 2 parts by volume water.

The amount of olefinic compound in the reaction mixture should exceed 0.5 mole per 100 moles of water and preferably 1–10 moles olefin per 100 moles of water while the iodine concentration can range between 75–140 mole percent of theoretical but it is preferred to make use of a 5–15% excess to maximize the yield.

The iodohydrin, with or without separation from the reaction mixture from the first reaction, is converted to the corresponding propylene oxide or other olefin oxide in the second reaction by removing hydrogen iodide from the iodohydrin. This is accomplished in the second reaction by increasing the pH by means of the addition of a buffer solution in the form of an alkaline solution which raises the pH to above 5 and preferably to a pH within the range of 6–10.5 while the temperature is reduced to within the range of 30°–90° C. The completeness of the conversion of the iodohydrin to the epoxide increases with increasing pH but it is undesirable to exceed a pH of 10.5.

As the agent for increasing the pH, it is preferred to make use of imidazole since the latter is employed in the formation of the catalyst complex used in the subsequent reaction for conversion of the ions of iodide to iodine, as will hereinafter be described. However, other alkalizing agents that do not precipitate iodide salts can be used, as represented by alkali metal carbonates such as sodium carbonate, and potassium carbonate; alkali metal oxides and hydroxides, such as lithium hydroxide, sodium hydroxide, sodium oxide, potassium hydroxide or oxide; alkaline earth metal oxides and hydroxides such as calcium hydroxide, barium hydroxide, barium oxide, aluminum oxide and hydroxides and mixtures thereof.

The second reaction to convert the iodohydrin to the olefin oxide and hydrogen iodide is carried out in an inert reaction solvent, such as a water-organic liquid mixture, such as used in the first reaction thereby permitting the conversion reaction to be carried out without separation of the iodohydrin from the first reaction mixture but merely by the addition of the basic buffer solution to raise the pH. Instead, use can be made of water mixed with other organic liquids, such as oxygen containing solvents represented by dioxane and tetrahydrofurane; nitrogen containing solvents such as nitriles represented by acetonitrile; and dialkyl amides such as dimethylformamide; or sulfur containing solvents such as sulfolane and dimethylsulfoxide. It is preferred to make use of a reduced amount of water with a minimum of 1 part by weight water to 300 parts by weight organic liquid. This may be accomplished by distilling off water from the first reaction.

The propylene epoxide that is formed is easily separated, as by distillation, from the reaction mixture.

The remaining solution of hydrogen iodide and spent buffer is processed by the third reaction to reconvert the iodide to iodine for recycle to the first iodohydrin forming reaction and to regenerate the buffer for recycling the buffer to the second reaction for conversion of the iodohydrin to the epoxide.

An important concept of this invention resides in carrying out the third reaction for oxidation of the iodide to iodine in the presence of a complex formed of copper ion and an azole, such as benzimidazole and preferably imidazole. It has been found to be desirable to make use of a copper catalyst with a ligand of the type described as a complexing agent, otherwise no detectable amount of oxidation of iodide occurs. The complexing agent also functions in the system to minimize and preferably prevent formation of solid CuI, insoluble copper hydroxide or copper oxide. Many other ligands other than imidazole and/or benzimidazole have been tried as the complexing agent in aqueous systems but with little if any success.

It is believed that, in the reaction $Cu^{++} + 2I^- \rightarrow CuI + \frac{1}{2}I_2$, the imidazole complexing agent keeps the $Cu^+$ in solution by complexing to form

which, in the presence of oxygen, promotes the electron transfer for the oxidation reaction.

The imidazole complexing agent should be present in an amount wherein the ratio in moles of imidazole to copper is greater than 2/1 and preferably in the ratio of 4–10 moles imidazole per mole of copper. The amount of catalyst can be selected to be within the range of 0.1–1 moles of catalyst per 1–2 moles of iodide.

Ordinarily, oxidation to convert the iodide to iodine is carried out at low pH of about 3 or less, with or without a copper catalyst. However, when use is made of the catalyst complex of copper and imidazole, the oxidation reaction to convert the iodides to iodine can be carried out at pH within the range of 5–10.5 and preferably 6–9.5. This enables the third reaction for conversion of the iodide to iodine to be carried out at about the same pH as exists during the second reaction with the result that the product of the second reaction can be used as the feed for the third reaction after the propylene oxide or other epoxide has been removed. Under such circumstances use can be made of a single reaction vessel for both the second and third reactions with means to distill or otherwise separate the epoxide, as shown in the flow diagram. By combining the second and third reactions, one obtains the buffer capacity of the imidazole in the copper complex for the second reaction and its catalyst function for the oxidation of the iodide in the third reaction. In effect, the reactions uniquely provide for any desired pH shift so that the two are advantageously combined, with the propylene oxide being carried off continuously as it is formed. Thus, the two reactions can be carried out concurrently by the continuous removal of epoxide as it is formed, while air is being bubbled through the reaction medium.

Recycle of the catalyst by retention through the sequence of reaction steps depends somewhat on the amount of neutralization required for pH control.

At high concentrations of iodide, two phases are formed identified as an aqueous phase and an organic phase. This enables easy extraction of the iodine that is formed in the organic phase. The separation is enhanced by the addition of an ether, such as butyl ether, which is incompatible with the mixture of organic solvent and water to enable separation of the iodine, even when iodide is present in insufficient concentrations to provide for phase separation between the water and organic phase.

In such instance where phase separation occurs between the water and the organic solvent, the iodine remains with the organic phase at the top to enable separation by decantation. Where the organic solvent and water remain in the same phase and an ether is added for separation, the iodine separates into the ether layer at the top while the organic solvent-water layer remains at the bottom to enable the iodine layer to be separated by decantation while the organic solvent can be separated from the remaining water layer by distillation. The heat given off in the exothermic first reaction can be used, if desired, to effect the distillation of organic solvent from the water remaining in the third reaction.

The use of acetonitrile will operate to shift the reaction equilibrium to give a higher concentration of iodine in the product of the third reaction (oxidation). When use is made of the combination of acetonitrile and toluene, the ratio of acetonitrile to toluene is not critical but it is preferred to make use of about 4 parts by volume acetonitrile per 1-2 parts by volume toluene.

By way of further modification, instead of extraction of the iodine with an ether, the desired extraction can be made with trimethylphenyl ammonium iodide. The latter dissolves in the aqueous solution and complexes with the iodine as it is formed for separation as a solid or liquid phase. Upon separation, the complex is readily reconverted to free iodine, as a vapor, and trimethylphenyl ammonium iodide, when heated to 120°-180° C.

There is reason to believe that, when the sodium nitrite or other catalyst heretofore employed for catalyzing the first reaction at low pH is replaced with the copper-imidazole complex catayst used in the third reaction for conversion of the iodide to iodine, the reaction of iodine with the olefin and water to form the iodohydrin need not be carried out at pH 3 or less and the catalyst is not consumed in the reaction. Instead the reaction proceeds in the normal manner at normal rate, without catalyst consumption or deterioration at pH levels within the range of 5-10.5.

This would be of considerable significance since this enables combination of all the reaction steps in a single reactor operating at a temperature within the range of 60°-90° C., into which propylene and oxygen in the form of oxygen gas, air or other oxygen containing gas are introduced as feed and propylene oxide is distilled off as product, depending on the control of reaction rates for equilizing the reaction rates to minimize excessive deviation of pH from within the range of 5-10.5.

The invention will now be illustrated by the following examples which are given by way of illustration and not by way of limitation.

EXAMPLE 1

Preparation of Catalyst

The catalyst mixture is prepared by stirring cuprous iodide and imidazole in an appropriate solvent in air. In one case, 0.30 g CuI and 0.43 g imidazole in 30 ml acetonitrile were stirred at room temperature to rapidly form a blue slurry of catalyst.

EXAMPLE 2

Preparation of Propylene Oxide and Iodine Regeneration in Sequential Reactions

Reaction I

Propylene iodohydrin is prepared in accordance with the method described in U.S. Pat. No. 3,548,012. A reactor was charged with 70 ml acetonitrile, 70 ml water, 14 g iodine, and 0.34 g sodium nitrite. This was heated to 70° C. and contacted with a 4:1 mixture of propylene and oxygen to produce 20 g propylene iodohydrin.

Reaction II

A buffered catalyst mixture was prepared by stirring 20.4 g CuI and 29.2 g imidazole in 300 ml acetonitrile and 1 ml water. To this was added 178 g KI. The resulting blue slurry had a pH of 10.6. The mixture was heated to 80° C., and 20 g propylene iodohydrin was added. During a 3 hour period, a solution of propylene oxide in acetonitrile was slowly distilled. The amount of epoxide present was 2.0 g (32% yield) as determined by titration of aliquots with sodium thiosulfate and acetic acid. The distillation was continued another 4 hours, during which time, another 0.5 g (8%) epoxide was recovered. At the end of this time, the pH was 8.9.

Reaction III

The mixture from reaction II was heated to 78° C. for 2 hours while bubbling air through it to cause the formation of iodine. The amount of iodine produced was 3.0 g, and the final pH was 9.6. During this process, an additional 0.2 g propylene oxide was recovered, bringing the total yield of epoxide to 43%.

EXAMPLE 3

Simultaneous Production of Propylene Oxide and Iodine

A 500 ml reaction flask was fitted with a tube for the introduction of gas bubbles into the reaction mixture; an addition funnel; a distilling head, condenser, and receiving flask assembly; and a cold trap cooled with dry ice and acetone through which exiting gases passed before leaving the system. Into the reaction flask were placed 2.9 g CuI, 300 ml acetonitrile, 25 g KI, and 4.1 g imidazole. Air was bubbled through the mixture for 1 hour to give a blue slurry of pH 10.5. The mixture, through which air was continuously bubbled, was heated to 65° C. Propylene iodohydrin (51.2 g) was added in portions. The temperature was gradually raised to 80° C. A mixture of propylene oxide and acetonitrile was recovered in the receiving flask and cold trap. The epoxide was determined by titration with sodium thiosulfate and acetic acid. The amount of epoxide recovered was 2.6 g, three times more than the molar amount of copper present. The amount of iodide produced was 8.6 g, equivalent to 4.5 times the molar amount of copper present.

The imidazole-copper complex is believed to comprise a new and novel catalyst for use in oxidation reactions, wherein the copper component is maintained in the complex to maintain the oxidizing function and to prevent its precipitation in an inactive form. This phenomenon of a stable oxidizing catalyst of the azole-copper complex, as represented by the imidazole-copper complex described, is demonstrated in such other oxidation reactions as in the conversion of phenol in water to hydroquinone with the introduction of air and in the presence of the imidazole-copper complex. These same reactions are not evidenced by copper alone or by imidazole alone. The imidazole-copper complex is unique from the standpoint of its retention of copper in the complex form where it can continue to function as a stable catalyst without precipitation in an inactive form.

We claim:

1. In a process for the production of epoxides from olefins comprising
    (a) wherein the olefin is reacted with iodine in the presence of water and a catalyst to yield iodohydrin and hydrogen iodide as a first reaction product,
    (b) adjusting the pH of the reaction product in the presence of a buffer to within the range of 5–10.5 and at a temperature within the range of 30°–90° C. to yield the epoxide and hydrogen iodide,
    (c) removing the epoxide from the reaction product of (b)
the improvement comprising
    (d) introducing an oxygen containing gas to oxidize the hydrogen iodide remaining in the reaction product of reaction (b) after the epoxide has been removed at a pH within the range of 5–10.5 and at a temperature within the range of 30°–90° C. in the presence of a catalyst of copper and an azole selected from the group consisting of imidazole and benzimidazole to convert the iodide to iodine,
    (e) recycling the iodine from reaction (d) to reaction (a).

2. The process as claimed in claim 1 in which the reaction (a) is carried out at a temperature within the range of 60°–90° C.

3. The process as claimed in claim 1 in which the reaction (a) is carried out in a solvent mixture of water and an organic liquid miscible with water and in which the olefin is soluble.

4. The process as claimed in claim 3 in which the organic liquid is selected from the group consisting of acetonitrile, dioxane, sulfolane, and dimethyl sulfoxide.

5. The process as claimed in claim 3 in which the organic liquid is present in an amount greater than 1–18 parts by volume per 2 parts by volume water.

6. The process as claimed in claim 3 in which the amount of olefin in the reaction mixture is greater than 0.5 mole per 100 moles water.

7. The process as claimed in claim 3 in which the olefin is present in the reaction mixture in an amount within the range of 1–10 moles olefin per 100 moles water.

8. The process as claimed in claim 1 in which the iodine is present in the reaction mixture in an amount within the range of 75–140 mole percent of theoretical up to 15% in excess thereof.

9. The process as claimed in claim 1 in which the increase in pH in reaction (b) is achieved by the addition of the buffer.

10. The process as claimed in claim 1 comprising introducing an imidazole into the product of reaction (a) to increase the pH for reaction of iodohydrin to the epoxide.

11. The process as claimed in claim 1 in which the reaction (b) to convert iodohydrin to the epoxide is carried out in an inert reaction solvent.

12. The process as claimed in claim 11 in which the inert reaction solvent is the same as the water organic liquid mixture of claim 3 whereby the reaction (b) can be carried out without separation of the iodohydrin from the reaction product of reaction (a).

13. The process as claimed in claim 11 in which the inert reaction solvent comprises a mixture of water with an organic liquid selected from the group consisting of an oxygen containing solvent, nitrogen containing solvents, dialkylamides, and sulfur containing solvents.

14. The process as claimed in claim 13 in which the water is present in the solvent mixture in an amount less than 1 part by weight per 300 parts by weight organic solvent liquid.

15. The process as claimed in claim 1 in which the epoxide is removed from the reaction mixture of step (c) by distillation.

16. The process as claimed in claim 1 in which the ratio of moles of azole to copper is greater than 2 to 1.

17. The process as claimed in claim 16 in which the ratio in moles of azole to copper is within the range of 4–10 moles of azole per mole of copper.

18. The process as claimed in claim 1 in which the catalyst in step (d) is present in an amount within the range of 0.1–1 moles catalyst per 1–2 moles iodide.

19. The process as claimed in claim 12 in which when the iodide is present in high concentration, the water-organic liquid mixture separates into an aqueous phase and an organic liquid phase with the iodine remaining in the organic phase.

20. The process as claimed in claim 19 which includes the addition of an ether to enhance phase separation.

21. The process as claimed in claim 1 in which the olefin is propylene with the corresponding production of propylene oxide as the epoxide.

22. The process as claimed in claim 1 in which the pH is adjusted in step (b) to within the range of 6–10.5.

23. The process as claimed in claim 1 in which the pH in step (d) is within the range of 6–9.5.

* * * * *